United States Patent
Shan et al.

(10) Patent No.: US 10,265,309 B2
(45) Date of Patent: Apr. 23, 2019

(54) SUBLINGUAL OPIOID FORMULATIONS CONTAINING NALOXONE

(71) Applicant: Insys Development Company, Inc., Chandler, AZ (US)

(72) Inventors: Ning Shan, Chandler, AZ (US); Rajesh R. Wakaskar, Chandler, AZ (US); Edwin A. Baldwin, Tempe, AZ (US); Andrew B. Schlinkert, Scottsdale, AZ (US); Min Wu, Chandler, AZ (US); Ningxin Yan, Chandler, AZ (US)

(73) Assignee: INSYS DEVELOPMENT COMPANY, INC., Chandler, AZ (US)

(*) Notice: Subject to any disclaimer, the term of this patent is extended or adjusted under 35 U.S.C. 154(b) by 18 days.

(21) Appl. No.: 15/606,146

(22) Filed: May 26, 2017

(65) Prior Publication Data

US 2017/0340620 A1 Nov. 30, 2017

Related U.S. Application Data

(60) Provisional application No. 62/442,045, filed on Jan. 4, 2017, provisional application No. 62/342,701, filed on May 27, 2016.

(51) Int. Cl.

| | | |
|---|---|---|
| *A61K 9/00* | (2006.01) |
| *A61K 47/10* | (2017.01) |
| *A61K 47/26* | (2006.01) |
| *A61K 31/485* | (2006.01) |
| *A61K 31/4468* | (2006.01) |
| *A61P 25/04* | (2006.01) |

(52) U.S. Cl.
CPC ......... *A61K 31/4468* (2013.01); *A61K 9/006* (2013.01); *A61K 31/485* (2013.01); *A61K 47/10* (2013.01); *A61K 47/26* (2013.01)

(58) Field of Classification Search
CPC .. A61K 31/4468; A61K 47/26; A61K 31/485; A61K 9/006; A61K 47/10
See application file for complete search history.

(56) References Cited

U.S. PATENT DOCUMENTS

| | | | | |
|---|---|---|---|---|
| 6,969,508 B2 * | 11/2005 | Dugger, III | ......... | A61K 9/0056 424/434 |
| 8,486,973 B2 * | 7/2013 | Kottayil | ............... | A61K 9/006 514/329 |
| 9,642,844 B2 * | 5/2017 | Kottayil | ............... | A61K 9/006 |
| 9,642,848 B2 * | 5/2017 | Amancha | ............... | A61K 47/10 |
| 9,839,611 B2 * | 12/2017 | Amancha | ............... | A61K 47/10 |
| 2006/0062812 A1 * | 3/2006 | Ross | ..................... | A61K 9/006 424/400 |

OTHER PUBLICATIONS

Edited by Rowe et al., (2009), Handbook of Pharmaceutical Excipients (6th ed.). London: APhA, (PhP) Pharmaceutical Press., pp. 592-594 and 786-789 (Year: 2009).*

* cited by examiner

*Primary Examiner* — My-Chau T. Tran
(74) *Attorney, Agent, or Firm* — Wood, Phillips, Katz, Clark & Mortimer

(57) ABSTRACT

Sublingual formulations containing an opioid, preferably, fentanyl or a pharmaceutically acceptable salt or ester thereof, naloxone or a pharmaceutically acceptable salt or ester thereof, and a terpene; as well as methods of treating pain by administering the formulations of the invention to a patient in need thereof.

2 Claims, 2 Drawing Sheets

SUBLINGUAL OPIOID FORMULATIONS CONTAINING NALOXONE

FIELD OF THE INVENTION

The invention is directed to sublingual formulations containing an opioid, preferably, fentanyl, and naloxone; and methods for treatment with the sublingual formulations.

BACKGROUND OF THE INVENTION

Opioids are substances that act on opioid receptors to produce morphine-like effects. Opioids are most often used medically to relieve pain. Opioids include opiates, an older term that refers to such drugs derived from opium, including morphine itself. Other opioids are semi-synthetic and synthetic drugs such as hydrocodone, oxycodone and fentanyl; antagonist drugs such as naloxone and endogenous peptides such as the endorphins.

Fentanyl is a μ-opioid receptor agonist with analgesic potency approximately 80-100 times that of morphine. In clinical settings, fentanyl exerts its principal pharmacologic effects on the central nervous system. Its primary actions are analgesic and sedation.

The analgesic effects of fentanyl are related to the blood level of the drug. In general, the minimum effective concentration and the concentration at which toxicity occurs rise with increasing tolerance to any and all opioids. The rate of development of tolerance may vary widely among individuals. All opioid mu-receptor agonists, including fentanyl, produce dose dependent respiratory depression. The risk of respiratory depression is typically less in patients receiving chronic opioid therapy who develop tolerance to respiratory depression and other opioid effects. Serious or fatal respiratory depression can occur, even at recommended doses, in vulnerable individuals.

Orally administered fentanyl is subject to first pass effect metabolism as upwards of 50% or more of orally administered fentanyl is not absorbed. Other forms of delivery such a parenteral, buccal, and transdermal have been utilized to decrease or avoid this first pass effect for fentanyl. Fentanyl is currently available in injectable form, as a lozenge (e.g. Actiq® (a registered trademark of Cephalon, Inc.)), as a transdermal system (e.g., Duragesic® (a registered trademark of Johnson & Johnson) 25, 50, 75, and 100 μg of fentanyl per hour) and a sublingual spray (e.g. Subsys®, a registered trademark of Insys Development Company, Inc.).

Naloxone has the following structure and is synthesized from thebaine:

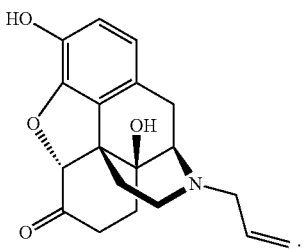

Naloxone is most commonly used to treat patients suffering from opioid dependence or overdose because it is a competitive μ-opioid antagonist that blocks the effects of opioids. Naloxone is currently available in Suboxone® (Suboxone is a registered trademark of Reckitt Benckiser Healthcare (UK) Limited) as tablet or sublingual film strip formulations. Suboxone® contains buprenorphine and naloxone in a 4:1 ratio.

One issue with other opioid dependence treatments is that they can become addictive. Naloxone, however, does not appear to be addictive and patients do not build up a tolerance.

Naloxone has also been used as a treatment for cognitive insensitivity to pain with anhidrosis. Insensitivity to pain with cognitive anhidrosis is a disorder in which the patient cannot feel pain.

Naloxone may be administered orally, intravenously, by injection or via the nasal mucosa. Naloxone has a low mean serum half-life when administered parentally. The quick metabolism may require repeat dosing or cause patient discomfort between doses. Enteral administration has low bioavailability due to hepatic first pass metabolism.

Naloxone is often administered to counteract the effect of fentanyl, for example to revive a patient after a fentanyl overdose. However, there is a need in the art for effective sublingual compositions comprising both an opioid, preferably, fentanyl, and naloxone so that naloxone could mitigate the effects of an opioid yet not block the clinical effect of the opioid. There is also a need in the art for formulations that would be opioid abuse deterrents.

SUMMARY OF THE INVENTION

In one aspect, the present invention is directed to a sublingual formulation comprising an opioid, naloxone or a pharmaceutically acceptable salt or ester thereof, and a terpene.

An opioid is preferably an opioid agonist.

The opioid agonist suitable for the purposes of the present invention include, but are not limited to, alfentanil, buprenorphine, butorphanol, codeine, diamorphine, dextromoramide, dezocine, dihydrocodeine, fentanyl, hydrocodone, hydromorphone, levorphanol, meperidine, meptazinol, methadone, morphine, nalbuphine, nalorphine, opium, oxycodone, oxymorphone, pentazocine, propoxyphene, remifentanyl, sufentanyl, tapentadol, and tramadol, and pharmaceutically acceptable salts thereof.

In one aspect, the present invention is directed to a sublingual formulation comprising fentanyl or a pharmaceutically acceptable salt or ester thereof, naloxone or a pharmaceutically acceptable salt or ester thereof, and a terpene.

Terpenes suitable for the purposes of the invention include menthol, limonene, linalool, cineole, nerolidol, farnesol, geraniol, carvone, terpinolene, and ascaridole.

Preferably, the sublingual formulation is an hydroalcoholic sublingual formulation.

Preferably, the hydroalcoholic sublingual formulation is a liquid spray sublingual formulation.

Preferably, the sublingual formulation also comprises menthol at a concentration from 0.25% to 10% w/w, wherein w/w refers to weight by weight of the total formulation.

Preferably, the terpene (for example, menthol) is present at a concentration from 0.25% to 10% w/w, wherein w/w refers to weight by weight of the total formulation.

The present invention further provides methods of treating pain by administering to a patient in need thereof a therapeutically effective amount of a composition of the present invention.

Preferably, an opioid is present at a concentration from 0.1% to 2.0% w/w, more preferably at a concentration from 0.1% to 1.6% w/w, and even more preferably at a concentration from 0.1% to 0.8% w/w, wherein w/w refers to weight by weight of the total formulation.

Preferably, fentanyl or the pharmaceutically acceptable salt or ester thereof is present at a concentration from 0.1% to 2.0% w/w, more preferably at a concentration from 0.1% to 1.6% w/w, and even more preferably at a concentration from 0.1% to 0.8% w/w, wherein w/w refers to weight by weight of the total formulation.

Preferably, naloxone or the pharmaceutically acceptable salt or ester thereof is present at a concentration from 0.1% to 2.0% w/w, more preferably 0.1% to 1.6% w/w, and even more preferably at a concentration from 0.1% to 0.8% w/w, wherein w/w refers to weight by weight of the total formulation.

The inventive formulations preferably include alcohol and propylene glycol. Alcohol is preferably dehydrated.

The preferred alcohol is ethanol.

Preferably, propylene glycol is present at a concentration from 1% to 20% w/w, more preferably 2% to 10% w/w, most preferably at a concentration from 4% to 6% w/w, wherein w/w refers to weight by weight of the total formulation.

Preferably, ethanol is present at a concentration from 20% to 80% w/w, more preferably 30% to 70% w/w, and most preferably at a concentration from 40% to 60% w/w, wherein w/w refers to weight by weight of the total formulation.

Preferably, the concentration of terpene (such as menthol) is from 0.025% to 10% w/w, more preferably, from 0.05% to 10% w/w, more preferably from 0.05% to 1% w/w, and even more preferably, 0.05 to 0.5% w/w, wherein w/w refers to weight by weight of the total formulation.

In some embodiments, the formulations of the invention comprise xylitol.

In one embodiment, the invention provides a sublingual spray formulation comprising fentanyl or a pharmaceutically acceptable salt or ester thereof at a concentration from 0.1% to 0.8% w/w, naloxone or the pharmaceutically acceptable salt or ester thereof is present at a concentration from 0.1% to 0.8% w/w, ethanol at a concentration from 40% to 60% w/w, propylene glycol at a concentration from 4% to 6% w/w, and menthol at a concentration from 0.025% to 10% w/w, wherein w/w refers to weight by weight of the total formulation.

The inventive formulations are stable, as determined by stability testing. Preferably, the inventive formulations contain no more than 0.06% of total fentanyl and naloxone impurities after four weeks at 55° C.

The inventive formulations preferably have a droplet size from 20 to 200 microns in diameter. In a more preferred embodiment, the droplet size is about 20 microns in diameter.

The inventive formulations may have different dosage strengths of fentanyl and naloxone. Some of the dosage strengths include, but are not limited to, 100 mcg, 200 mcg, 400 mcg, 600 mcg, 800 mcg, 1200 mcg and 1600 mcg. Further, the invention contemplates that different strengths may come in different dosage forms. For example, one strength can be administered in more than one dose.

The mass ratio of dose between an opioid (preferably, fentanyl) and naloxone varies from 4:1 to 1:2.

Preferably, the inventive formulations, when administered to humans, result in pain relief less than 5 minutes after sublingual administration, more preferably, less than 4 minutes after sublingual administration, and even more preferably, less than 3 minutes after sublingual administration.

Preferably, after the provided formulations are administered sublingually to patients in need thereof, plasma concentrations of naloxone are lower than the therapeutic concentration of naloxone, resulting in only the limited systemic exposure to naloxone.

Further, in some embodiments, the present invention provides formulations that serve as opioid abuse deterrents, and more preferably, a fentanyl abuse-deterrent.

In certain embodiments, the present invention is directed to a method of treating pain comprising administering to a patient in need thereof a therapeutically effective amount of a composition of the present invention. Pain indications include, but are not limited to, shock, limb amputation, severe chemical or thermal burn injury, sprains, ligament tears, fractures, wounds and other tissue injuries, dental surgery, procedures and maladies, labor and delivery, during physical therapy, pre- and post-operative pain, radiation poisoning, cancer, acquired immunodeficiency syndrome (AIDS), epidural (or peridural) fibrosis, back surgery and laminectomy, sciatica, painful sickle cell crisis, arthritis, autoimmune disease, intractable bladder pain, and the like Preferably, the pain is breakthrough pain or postoperative pain. Even more preferably, the pain is cancer pain.

DETAILED DESCRIPTION OF THE INVENTION

Figure 1:
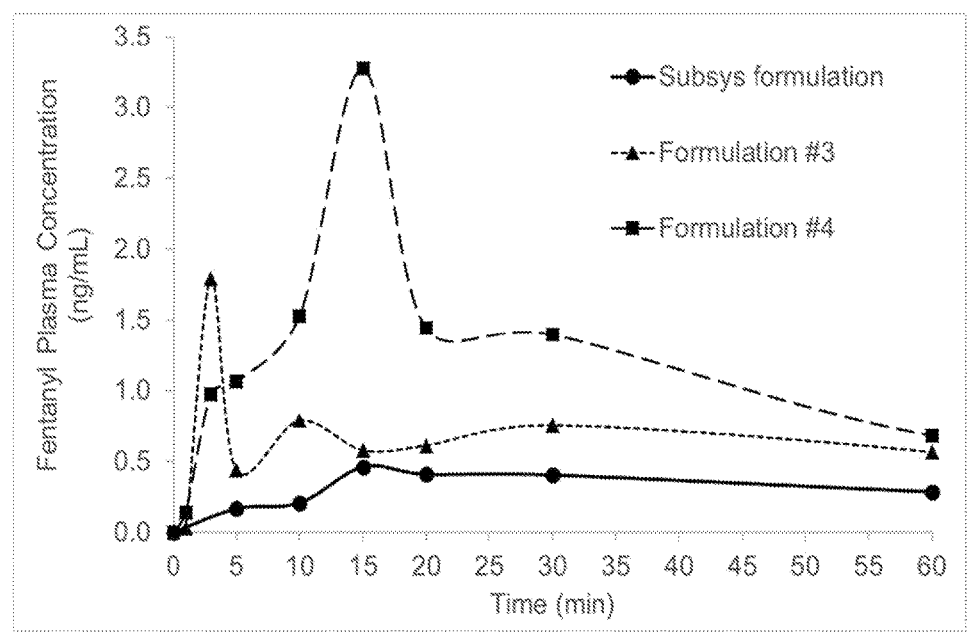
FIG. 1 is a chart of fentanyl plasma concentration versus time after administration of various fentanyl-naloxone formulations.
Figure 2:
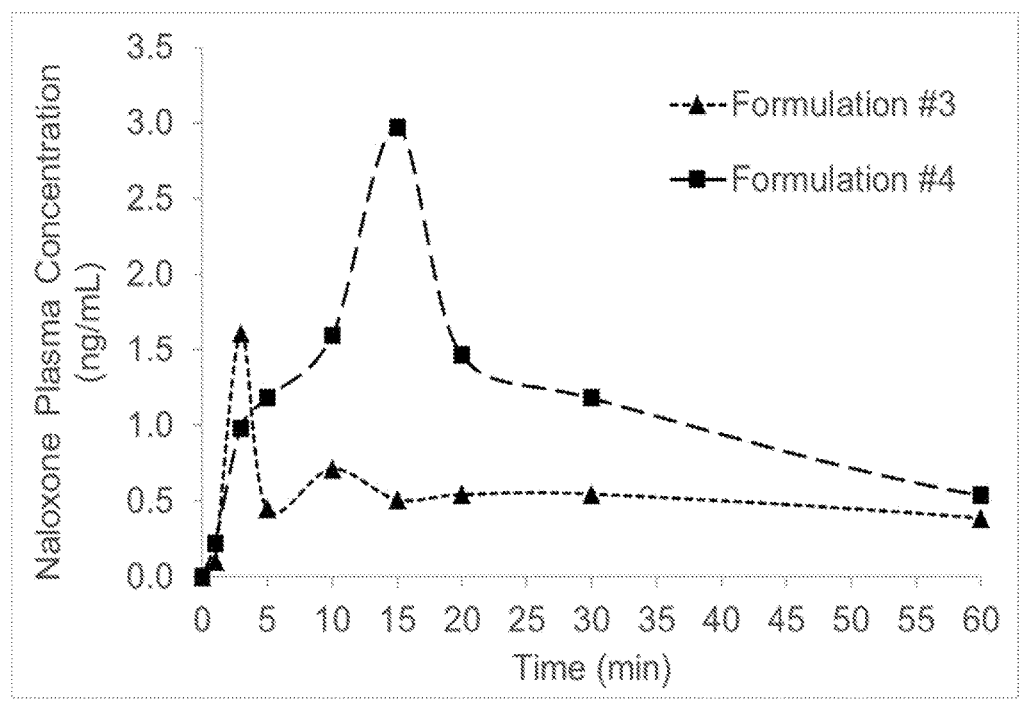
FIG. 2 is a chart of naloxone plasma concentration versus time after administration of various fentanyl-naloxone formulations.

The present invention is directed to a sublingual formulation comprising an opioid, naloxone or a pharmaceutically acceptable salt or ester thereof and a terpene. Preferably, the sublingual formulation is a spray sublingual formulation.

An opioid is preferably an opioid agonist.

The opioid agonists suitable for the purposes of the present invention include, but are not limited to, alfentanil, buprenorphine, butorphanol, codeine, diamorphine, dextromoramide, dezocine, dihydrocodeine, fentanyl, hydrocodone, hydromorphone, levorphanol, meperidine, meptazinol, methadone, morphine, nalbuphine, nalorphine, opium, oxycodone, oxymorphone, pentazocine, propoxyphene, remifentanyl, sufentanyl, tapentadol, and tramadol, and pharmaceutically acceptable salts thereof.

In a preferred embodiment, the opioid agonist is fentanyl or a pharmaceutically acceptable salt or ester thereof.

In one aspect, the present invention is directed to a sublingual formulation comprising fentanyl or a pharmaceutically acceptable salt or ester thereof, naloxone or a pharmaceutically acceptable salt or ester thereof, and a terpene.

Terpenes suitable for the purposes of the invention include menthol, limonene, linalool, cineole, nerolidol, farnesol, geraniol, carvone, terpinolene, and ascaridole.

Preferably, the sublingual formulation is an hydroalcoholic sublingual formulation.

Preferably, the hydroalcoholic sublingual formulation is a liquid spray sublingual formulation.

A terpene (such as menthol) is preferably present at a concentration from 0.025% to 10% w/w, and more preferably at least 0.05% to 0.5% w/w, wherein w/w refers to weight by weight of the total formulation.

The inventive formulations preferably include alcohol and propylene glycol. Alcohol is preferably dehydrated.

The preferred alcohol is ethanol.

The present invention further provides methods of treating pain by administering to a patient in need thereof a therapeutically effective amount of a composition of the present invention.

A surprising and unexpected effect has been found that an opioid (preferably, fentanyl) and naloxone, when present in a sublingual formulation, preferably, an hydroalcoholic formulation and even more preferably an liquid spray formulation, provide effective pain relief to a patient. Another advantage of the provided formulations is that both an opioid (preferably, fentanyl) and naloxone are present in one formulation, obviating the need for a patient to take the opioid and naloxone separately.

Further, in one embodiment, the combination formulation is an opioid abuse deterrent, and preferably, a fentanyl abuse deterrent, as it deters abuse of an opioid such as fentanyl. The observed plasma concentrations of naloxone is expected to be lower than the therapeutic concentration of naloxone, and therefore, the limited systemic exposure of naloxone after sublingual administration would not affect the clinical performance of an opioid, such as fentanyl. The sublingual administration of opioid/naloxone (preferably, fentanyl/naloxone) combination formulation is preferred to intravenous administration, because if the combination formulation is administered intravenously, it is expected that the systemic exposure of naloxone would block the clinical effect of an opioid (such as fentanyl).

The provided formulations include a terpene, wherein terpene is present at concentrations from 0.025% to 10% w/w.

The sublingual formulations of the present invention are useful in the treatment of moderate to severe pain. Preferably the sublingual formulations of the present invention are useful for the treatment of breakthrough pain, and even more preferably, for the treatment of cancer pain. For example, the formulations of the present invention are preferably suitable for a patient receiving chronic pain therapy who experiences breakthrough pain and is in need of acute pain relief.

The sublingual formulations of the present invention may be used to alleviate pain from many causes, including but not limited to shock, limb amputation, severe chemical or thermal burn injury, sprains, ligament tears, fractures, wounds and other tissue injuries, dental surgery, procedures and maladies, labor and delivery, during physical therapy, postoperative pain, radiation poisoning, cancer, acquired immunodeficiency syndrome (AIDS), epidural (or peridural) fibrosis, back surgery and laminectomy, sciatica, painful sickle cell crisis, arthritis, autoimmune disease, intractable bladder pain, and the like. Sublingual administration of the formulations of fentanyl, a pharmaceutically acceptable salt thereof, or derivative thereof, of the present invention is also preferably amenable to hospice use, particularly hospices that specialize in the care of cancer and AIDS patients.

In certain preferred embodiments, the sublingual administration of the inventive formulations can relieve or alleviate episodes of acute breakthrough pain that can occur in a chronic pain condition. The inventive formulations can also be used as an adjunct therapy to a conventional treatment regimen for a chronic pain condition to alleviate breakthrough pain. In certain embodiments, the inventive formulations can be used as an anesthetic premedication, for the induction of anesthesia, for use as a sedative and/or for the treatment of anxiety.

The inventive formulations may be particularly beneficial in the patient with cancer who is unable to tolerate oral administration because of nausea and vomiting, dysphagia as a result of disease, or parenteral administration because of decreased venous access, emaciation, or coagulation defects. The inventive formulations preferably have potential advantages of even greater ease of use and rapid onset of pain relief action than existing fentanyl sublingual spray formulations.

The inventive formulations can preferably be delivered by sublingual spray devices.

The sublingual administration of an opioid, such as fentanyl, a pharmaceutically acceptable salt or an ester thereof, is advantageous over other forms of administration in that it does not require injection using a syringe and needle, it avoids necrosis that can accompany intramuscular (i.m.) administration of drugs, and it avoids the need to constantly suck on a lozenge or lollipop. Preferably, the inventive formulations are suitable for self-administration.

Definitions

As used herein, all numerical values relating to amounts, weights, and the like, are defined as "about" each particular value, that is, plus or minus 10%. For example, the phrase "10% w/w" is to be understood as "9% to 11% w/w." Therefore, amounts within 10% of the claimed value are encompassed by the scope of the claims.

As used herein "% w/w" refers to the weight percent by weight of the total formulation.

As used herein "% w/v" refers to the weight percent by volume of the total formulation.

As used herein the term "effective amount" refers to the amount necessary to treat a patient in need thereof.

As used herein the term "patient" refers but is not limited to a person that is being treated for pain or another affliction or disease that can be treated with fentanyl.

As used herein the term "breakthrough pain" refers to a pain that exceeds a threshold in a patient which causes cognizable discomfort wherein the pain experienced by the patient is otherwise typically controlled e.g., by chronic analgesic therapy, and tolerated. For example, pain related to medical illnesses, such as cancer, typically fluctuates, and patients often report the experience of cognizable discomfort (e.g., breakthrough pain).

As used herein the term "pharmaceutically acceptable" refers to ingredients that are not biologically or otherwise undesirable in a sublingual dosage form.

The term "opioid" refers to any substance that acts on opioid receptors to produce morphine-like effects. It does not include opioid antagonists that do not activate the receptors, such as naloxone and naltrexone.

The term "opioid agonist" refers to substances that bind to the opioid receptors and provide pain relief. It includes both full and partial agonists, such as nalorphine and levallorphan.

Pharmaceutically acceptable salts of opioids and naloxone that can be used in accordance with the current invention include but are not limited to hydrochloride, dihydrate hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

Compositions of the Invention

An opioid used in the present invention may be in the form of an acid, free base or salt. A preferred concentration range of an opioid suitable for the present invention is from 0.1% to 2% w/w, more preferably from 0.1 to 1.6% w/w, and even more preferably from 0.1% to 0.8% w/w.

Fentanyl used in the present invention may be in the form of an acid, free base or salt. Derivatives of fentanyl suitable for use in the present invention include, but are not limited to, sufentanil, carfentanil, lofentanil, alfentanil, or the like. A preferred concentration range of fentanyl suitable for the present invention is from 0.1% to 2% w/w, more preferably from 0.1 to 1.6% w/w, and even more preferably from 0.1% to 0.8% w/w.

Naloxone used in the present invention may be in the form of an acid, free base or salt. The preferred salt is HCl dihydrate. A preferred concentration range of naloxone suitable for the present invention is from 0.1% to 2.0% w/w, more preferably from 0.1 to 1.6% w/w, and even more preferably from 0.1% to 0.8% w/w.

The inventive formulations preferably include alcohol and propylene glycol. Alcohol is preferably dehydrated.

The preferred alcohol is ethanol.

Alcohol, and in particular, ethanol, is present preferably at concentration from 40% to 60% w/w; and propylene glycol is present preferably at a concentration from 4% to 10%; and more preferably, from 4% to 6% w/w.

The formulations of the invention can include additional solvents, which include, but are not limited to, methanol, propyl alcohol, butyl alcohol, glycerol, butylene glycol, polyethylene glycols such as polyethylene glycol ("PEG") 200 and PEG 400 and the like. Mixtures of any of the aforementioned solvents may be used. In certain embodiments, the solvent is a non-polar hydrocarbon, preferably a $C_{7-18}$ hydrocarbon of a linear or branched configuration, its alcohols, fatty acid esters, and triglycerides, such as miglyol.

A terpene (such as menthol) is present at concentrations from 0.025% to 10% w/w, preferably, from 0.05% to 10% w/w, more preferably, from 0.05% to 1% w/w, and even more preferably at 0.05 to 0.5% w/w.

Sweetening agents suitable for use in the present invention include, but are not limited to, sucralose, aspartame, mannitol, saccharin, xylitol, and the like. In certain preferred embodiments, the sweetening agent is xylitol. A preferred concentration range of sweetening agents suitable for the present invention is from 0.001% to 10% w/w, preferably in an amount from 0.01% to 5% w/w, and even more preferably 3% w/w.

The inventive formulations are stable, as determined by stability testing. Preferably, the inventive formulations contain no more than 0.06% of total fentanyl and naloxone impurities, after four weeks at 55° C.

The inventive formulations are preferably aqueous sprays.

The inventive formulations preferably have a droplet size from 20 to 200 microns in diameter. In a more preferred embodiment, the droplet size is about 20 microns in diameter.

The inventive formulations may have different dosage strengths of an opioid (such as fentanyl) and naloxone. Some of the dosages include, but are not limited to, 100 mcg, 200 mcg, 400 mcg, 600 mcg, 800 mcg, 1200 mcg and 1600 mcg. The invention contemplates that different strengths may be administered through different dosages. For example, one strength may be administered through more than one dosages.

In certain embodiments, the invention provides opioid/naloxone (such as fentanyl/naloxone) sublingual spray formulations exhibiting a mean maximum plasma concentration ($C_{max}$) of about 1.0 ng/ml±1.6 based on a sublingual dose of about 200 mcg fentanyl when administered sublingually to Yucatan mini-pigs.

In certain embodiments, the invention provides opioid/naloxone (such as fentanyl/naloxone) sublingual spray formulations providing a mean time to maximum plasma concentration ($T_{max}$) of about 15 minutes when administered sublingually to Yucatan mini-pigs.

In certain embodiments, the invention provides opioid/naloxone (such as fentanyl/naloxone) sublingual spray formulations providing an area under the plasma concentration time curve to 24 hours ($AUC_{0-24\,h}$) of about 90.8±1.6 ng*min/mL when administered sublingually to Yucatan mini-pigs.

Preferred Embodiments

In one preferred embodiment, the present invention is directed to a sublingual spray formulation comprising 0.244% w/w fentanyl base, 0.298% naloxone HCl dihydrate, 54.5% ethanol ("EtOH"), 4.95% w/w propylene glycol ("PG"), 0.5% w/w menthol, 2.97% xylitol, 0.001% disodium edetate (EDTA) and 36.55% water. This formulation preferably has a fentanyl $T_{max}$ of 3 min; a fentanyl $C_{max}$ of 1.8 ng/mL and a fentanyl $AUC_{0-24\,h}$ of 135.6 ng*min/mL, after a single-dose sublingual spray administration in minipigs.

In another preferred embodiment, the present invention is directed to a sublingual spray formulation comprising 0.488% w/w fentanyl base, 0.596% naloxone HCl dihydrate, 54.5% ethanol ("EtOH"), 4.95% w/w propylene glycol ("PG"), 0.5% w/w menthol, 2.97% xylitol, 0.005 disodium edetate (EDTA) and 35.99% water. This formulation preferably has a fentanyl $T_{max}$ of 10 min; a fentanyl $C_{max}$ of 3.5 ng/mL and a fentanyl $AUC_{0-24\,h}$ of 217 ng*min/mL, after a single-dose sublingual spray administration in minipigs.

The following Examples are provided solely for illustrative purposes and are not meant to limit the invention in any way.

EXAMPLES

Example 1: Preparation of Novel Fentanyl-Naloxone Combination Formulation

Sublingual spray formulations were created by first degassing ethanol and USP purified water separately. Soluble excipients were then dissolved in either ethanol or purified water based on their solubility. Next, the above solutions were combined. For Subsys®, fentanyl was added to the final solution and mixed until dissolved. For the combination formulation #1, naloxone hydrochloride dihydrate and fentanyl were added to the final solution and mixed until dissolved.

In a single administration of the combination formulation, the doses of fentanyl and naloxone range from 100 to 1600 μg (fentanyl equivalent and naloxone equivalent), while the mass ratio of dose between fentanyl and naloxone varies between 1:0.5 and 1:2. The ideal mass ratio of dose between fentanyl and naloxone is 1:1.

TABLE 1

Subsys® and Fentanyl-Naloxone Combination Sublingual Spray Formulations for minipig studies.

| Component | Subsys® Formulation | Formulation #1 | Formulation #2 | Formulation #3 | Formulation #4 |
|---|---|---|---|---|---|
| Fentanyl Base | 0.244 | 0.244 | 0.244 | 0.244 | 0.488 |
| Naloxone HCl Dihydrate | — | — | — | 0.298 | 0.596 |
| Dehydrated Alcohol | 54.5 | 54.5 | 54.5 | 54.5 | 54.5 |
| Propylene Glycol | 4.945 | 4.945 | 4.945 | 4.945 | 4.945 |
| L-Menthol | 0.05 | 0.5 | 0.5 | 0.5 | 0.5 |
| Xylitol | 2.967 | 2.967 | 2.967 | 2.967 | 2.967 |
| Disodium Edetate | — | — | 0.001 | 0.001 | 0.005 |
| Purified water | 37.294 | 36.844 | 36.843 | 36.545 | 35.999 |
| Total | 100 | 100 | 100 | 100 | 100 |
| pH | No pH adjustment | No pH adjustment | Adjusted the pH to 4 using dil. HCl | Adjusted the pH to 4 using dil. HCl | Adjusted the pH to 4.5 using dil. HCl |

Values = % w/w

Example 2: Minipig Pharmacokinetic Data for Fentanyl-Naloxone Combination Formulation Protocol design was a single dose crossover study. Five to six healthy male Yucatan minipigs weighing approximately forty kilograms each were sublingually administered Subsys® formulation or fentanyl-naloxone combination formulations. The minipigs were fasted overnight till four hours post administration. Each dosing was followed by a one-week washout period. Blood samples were taken prior to administration and 1, 3, 5, 10, 15, 20, 30 min, 1, 1.5, 2, 3, 4, 5 and 24 hours post dose. Minipig plasma samples were measured for fentanyl and naloxone concentrations via liquid chromatography-tandem mass spectrometry.

The following pharmacokinetic parameters were calculated: peak concentration in plasma ($C_{max}$), time to reach $C_{max}$ ($T_{max}$), and area under the concentration-time curve from time-zero to 24 hours postdose ($AUC_{0-24\ h}$).

At 5 minutes after a single-dose sublingual administration of Subsys® in minipigs, the geometric mean plasma concentration of fentanyl was 0.17 ng/mL. With the menthol concentration in the subsequent formulations increased to 0.5%, this enabled a much more rapid absorption of fentanyl. Specifically, the combination formulations (Formulation 3 and 4) exhibited mean plasma fentanyl concentrations of 0.44 ng/mL and 0.34 ng/mL at 5 minutes postdose, respectively. It was also noted that a mean plasma fentanyl concentration of 1.79 and 0.49 ng/mL was achieved as early as 3 minutes after sublingual administration of the combination formulations (Formulation 3 and 4). In addition, the combination Formulation 3 (200 μg dose, pH 4) showed an approximately 3.6-fold increase in $C_{max}$ and an approximately 2-fold increase in $AUC_{0-24\ h}$, as compared to Subsys®.

The pharmacokinetic profile of naloxone after sublingual administration of the combination formulation was also evaluated. The plasma concentration of naloxone reached the peak concentration of 1.61 ng/mL for Formulation 3 (200 μg dose, pH 4), at 3 min post-dose and quickly declines due to fast metabolism of naloxone in vivo. Specifically, the geometric mean plasma concentrations of naloxone decreased to 0.51 and 0.55 ng/mL at 15 min and 30 min postdose, respectively for Formulation 3. However, for Formulation 4 (400 μg dose, pH 4.5), there is a steady increase in naloxone concentration, until a peak concentration of 2.97 ng/mL is attained at 15 min post-dose.

Based on the current minipig data, it is expected that the observed plasma concentrations of naloxone to be lower than the therapeutic concentration of naloxone, and therefore, the limited systemic exposure of naloxone after sublingual administration would not affect the clinical performance of fentanyl. However, when the fentanyl-naloxone combination product is administered intravenously, we expect that the systemic exposure of naloxone would block the clinical effect of fentanyl.

TABLE 2

Geometric mean plasma concentrations for Fentanyl after sublingual administration of 200 or 400 μg single-doses of fentanyl in Fentanyl or Fentanyl-Naloxone combination formulation (see Table 1) to Yucatan minipigs under fasted conditions.

| Parameter | Subsys® Formulation | Formulation #1 | Formulation #2 | Formulation #3 | Formulation #4 |
|---|---|---|---|---|---|
| N | 6 | 5 | 5 | 5 | 5 |
| Concentration @ 1 min (ng/mL) | NC | NC | 0.21 | 0.03 | 0.14 |
| Concentration @ 3 min (ng/mL) | NC | 0.63 | 0.59 | 1.79 | 0.97 |
| Concentration @ 5 min (ng/mL) | 0.17 | 0.37 | 0.56 | 0.44 | 1.07 |

TABLE 2-continued

Geometric mean plasma concentrations for Fentanyl after sublingual administration of 200 or 400 µg single-doses of fentanyl in Fentanyl or Fentanyl-Naloxone combination formulation (see Table 1) to Yucatan minipigs under fasted conditions.

| Parameter | Subsys ® Formulation | Formulation #1 | Formulation #2 | Formulation #3 | Formulation #4 |
|---|---|---|---|---|---|
| Concentration @ 10 min (ng/mL) | 0.21 | 0.43 | 0.80 | 0.79 | 1.53 |
| Concentration @ 15 min (ng/mL) | 0.46 | 0.57 | 0.66 | 0.58 | 3.28 |
| Concentration @ 30 min (ng/mL) | 0.40 | 0.51 | 0.55 | 0.76 | 1.40 |
| $T_{max}$ (min) | 15 | 15 | 10 | 3 | 10 |
| $C_{max}$ (ng/mL) | 0.5 ± 2.0 | 1.0 ± 1.6 | 1.2 ± 1.7 | 1.8 ± 2.3 | 3.5 ± 2.6 |
| $AUC_{0-24\,h}$ (ng*min/mL) | 68.2 ± 1.4 | 90.8 ± 1.6 | 119 ± 1.3 | 135.6 ± 1.6 | 217.0 ± 1.7 |

NC: blood sample not collected
N: Number of animals used
$T_{max}$: median value
$C_{max}$ and $AUC_{0-24h}$: geometric mean ± geometric SD

TABLE 3

Geometric mean plasma concentrations for Naloxone after sublingual administration of 200 or 400 µg single-dose of naloxone hydrochloride in Fentanyl-Naloxone combination formulation (see Table 1) to Yucatan minipigs under fasted conditions.

| Parameter | Formulation #3 | Formulation #4 |
|---|---|---|
| N | 5 | 5 |
| Concentration @ 1 min (ng/mL) | 0.11 | 0.22 |
| Concentration @ 3 min (ng/mL) | 1.61 | 0.98 |
| Concentration @ 5 min (ng/mL) | 0.45 | 1.18 |
| Concentration @ 10 min (ng/mL) | 0.71 | 1.59 |
| Concentration @ 15 min (ng/mL) | 0.51 | 2.97 |
| Concentration @ 30 min (ng/mL) | 0.55 | 1.18 |
| $T_{max}$ (min) | 3 | 10 |
| $C_{max}$ (ng/mL) | 1.7 ± 2.9 | 3.6 ± 2.4 |
| $AUC_{0-24\,h}$ (ng*min/mL) | 65.0 ± 2.0 | 132.6 ± 1.8 |

$T_{max}$: median value
$C_{max}$ and $AUC_{0-24\,h}$: geometric mean ± geometric SD
N: Number of animals used

What is claimed is:

1. A sublingual spray formulation comprising fentanyl or a pharmaceutically acceptable salt or ester thereof at a concentration from 0.1% to 2% w/w, naloxone or a pharmaceutically acceptable salt or ester thereof at a concentration from 0.1% to 2% w/w, ethanol at a concentration from 40% to 60% w/w, propylene glycol at a concentration from 4% to 6% w/w, and menthol at a concentration from 0.05% to 10% w/w, wherein w/w refers to weight by weight of the total formulation.

2. A method of treating pain comprising administering to a patient in need thereof a therapeutically effective amount of a formulation of claim 1.

* * * * *